United States Patent

Sidi et al.

[11] 3,962,271
[45] June 8, 1976

[54] MONOCYCLIC POLYOXYMETHYLENEOXAZOLIDINES AND BIOCIDAL COMPOSITIONS CONTAINING SAME

[75] Inventors: Henri Sidi, Paramus; Hilding R. Johnson, Wayne, both of N.J.

[73] Assignee: Tenneco Chemicals, Inc., Saddle Brook, N.J.

[22] Filed: Oct. 31, 1974

[21] Appl. No.: 519,884

Related U.S. Application Data

[62] Division of Ser. No. 447,797, March 4, 1974, Pat. No. 3,890,264.

[52] U.S. Cl. ............................................ 260/307 FA
[51] Int. Cl.² ...................................... C07D 263/06
[58] Field of Search ............................... 260/307 FA

[56] References Cited
UNITED STATES PATENTS

| | | | |
|---|---|---|---|
| 2,571,985 | 10/1951 | Carnes | 260/307 |
| 3,502,627 | 3/1970 | Du Pont | 260/86.1 |

Primary Examiner—Raymond V. Rush
Attorney, Agent, or Firm—Evelyn Berlow

[57] ABSTRACT

Biocidal compositions useful in controlling the growth of bacteria and fungi in aqueous surface-coating compositions are aqueous solutions that contain from 20 percent to 80 percent by weight of a monocyclic polyoxymethyleneoxazolidine having the structural formula

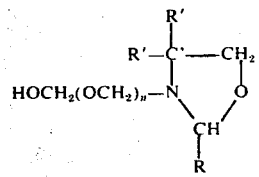

wherein R represents hydrogen, alkyl of 1 to 6 carbon atoms, phenyl, halophenyl, or $-(CH_2O)_mCH_2OH$; each R' represents alkyl of 1 to 6 carbon atoms or $-CH_2OH$; m represents a number in the range of 0 to 2; and n represents a number in the range of 1 to 4. The polyoxymethyleneoxazolidines preferably contain a total of not more than six oxymethylene units ($-CH_2O-$) in one or more ring substituents.

4 Claims, No Drawings

MONOCYCLIC POLYOXYMETHYLENEOXAZOLIDINES AND BIOCIDAL COMPOSITIONS CONTAINING SAME

This is a division of our copending application Ser. No. 447,797, which was filed on Mar. 4, 1974 and which is now U.S. Pat. No. 3,890,264.

This invention relates to certain monocyclic polyoxymethyleneoxazolidines. It further relates to biocidal compositions that are aqueous solutions which contain from 20 to 80 percent by weight of these polyoxymethyleneoxazolidines and which are useful in controlling the growth of bacteria and fungi in aqueous surface-coating compositions.

It is well known in the art that paints and varnishes often have inadequate resistance to the action of microorganisms. Some of these coating compositions, such as enamels and house paints, contain as their resinous binders drying oils, oleoresinous varnishes, or alkyd resins, which are subject to attack by fungi and bacteria. Others, for example, aqueous dispersions of water-insoluble synthetic linear polymers, generally contain as plasticizers and thickeners materials that have their origin in animal or vegetable sources and that render the compositions susceptible to mildew. The resulting deterioration of the surface-coating compositions seriously hinders their full scale utilization, particularly in those areas and in those applications that are conducive to such attack.

Various biocidal materials have been suggested for use in surface-coating compositions, but none has proven entirely satisfactory in this application. Some do not provide the required prolonged protection against attack by microorganisms, while others undergo sulfide staining and still others hydrolyze in alkaline aqueous paint systems or separate from the applied coating by migration, volatilization, or leaching after the coating has been spread in a thin layer over the surface to be protected. Some biocidal materials cause the coating compositions to gel or impart color or odor to them.

This invention relates to biocides that are of particular value in surface-coating compositions. These biocides, which are stable in aqueous solutions, which are thoroughly compatible with the resinous binders that commonly are used in surface-coating compositions and which are resistant to sulfide staining, provide excellent and prolonged resistance to deterioration resulting from attack by bacteria, fungi, and other microorganisms without adversely affecting the color, pH, viscosity, and other physical properties of the surface-coating compositions.

The biocidal compounds of this invention have the structural formula

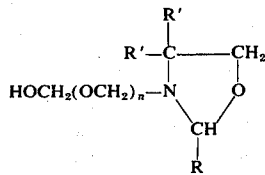

wherein R represents hydrogen, alkyl of 1 to 6 carbon atoms, phenyl, halophenyl, or $-(CH_2O)_mCH_2OH$; each R' represents alkyl of 1 to 6 carbon atoms or $-CH_2OH$; m represents a number in the range of 0 to 2; and n represents a number in the range of 1 to 4.

Illustrative of these monocyclic polyoxymethyleneoxazolidines are the following: 3-hydroxymethyloxymethylene-4,4-dimethyloxazolidine; 3-[hydroxymethyl-di(oxymethylene)]-4,4-diethyloxazolidine, 3-[hydroxymethyl-tri(oxymethylene)]-4,4-diethyloxazolidine, 3-[hydroxymethyl-tetra(oxymethylene)]-4-methyl- 4-isopropyloxazolidine, 2-hexyl-3-[hydroxymethyl-tri(oxymethylene)]- 4,4-di(hydroxymethyl)oxazolidine, 2phenyl-3-[hydroxymethyl-di(oxymethylene)]-4-hexyl-4-hydroxymethyloxazolidine, 2-p-chlorophenyl -3-(hydroxymethyloxymethylene)-4,4-di(hydroxymethyl)oxazolidine, 2-hydroxymethyl-3-[hydroxymethyl-di(oxymethylene)]-4,4-dibutyloxazolidine, and 2,3-bis(hydroxymethyloxymethylene)-4,4-dimethyloxazolidine.

The preferred compounds for use in surface-coating compositions are those in which the total number of oxymethylene ($-CH_2O-$) units in one or more of the substituents on the oxazolidine ring is not greater than six. While compounds having more than six oxymethylene units in their ring substituents are very effective in controlling the growth of bacterial and fungi, they tend to be somewhat unstable in surface-coating compositions and to impart to them the odor of formaldehyde. Examples of the preferred monocyclic compounds include polyoxymethyleneoxazolidines in which i. the substituent in the 2-position is hydrogen, alkyl, phenyl, or halophenyl, that in the 3-position is $-(CH_2O)_{1-4}-CH_2OH$, and those in the 4-position are alkyl;

ii. the substituent in the 2-position is $-(CH_2O)_{0-3}CH_2OH$, that in the 3-position is $-CH_2OCH_2OH$, and those in the 4-position are alkyl; and iii. the substituent in the 2-position is $-CH_2OH$, that in the 3-position is $-(CH_2O)_{1-2}CH_2OH$, and one or both of those in the 4-position are $-CH_2OH$.

The biocidal compounds of this invention may be prepared by any suitable and convenient procedure. For example, they may be prepared by the reaction of the appropriate oxazolidine with formaldehyde and/or paraformaldehyde. Alternatively, they may be prepared by the reaction of an aminoalcohol with formaldehyde and/or paraformaldehyde and optionally another aldehyde. These reactions are ordinarily carried out in aqueous solution at a temperature between about 20°and 100°C. When an aqueous formaldehyde solution is used, the reactions are preferably carried out at ambient temperature; when paraformaldehyde or a mixture of aqueous formaldehyde and paraformaldehyde is used, it is preferred that the reaction be carried out at a higher temperature.

Among the aminoalcohols that can be reacted with formaldehyde and, if desired, another aldehyde to form the novel polyoxymethyleneoxazolidines are 2-amino-2-methylpropanol-1, 2-amino-2-ethylpropanol-1, 2-amino-2-methyl-1,3-propanediol, 2-amino-2-ethyl-1,3-propanediol, 2-amino-2-butyl-1,3-propanediol, and tris(hydroxymethyl)aminomethane. The aminoalcohol is reacted with formaldehyde or a mixture of formaldehyde and a second aldehyde. The second aldehyde may be an aliphatic aldehyde, such as acetaldehyde, α-chloroacetaldehyde, propionaldehyde, butyraldehyde, or 2-ethylbutyraldehyde; an aromatic aldehyde, such as benzaldehyde, p-chlorobenzaldehyde, or 2,4-dichlorobenzaldehyde; a dialdehyde, such as glyoxal, succinaldehyde, or glutaraldehyde; or a mixture of these aldehydes.

The reaction products may be recovered from the aqueous solutions in which they are formed and purified by known techniques. In most cases the products are mixtures comprising polyoxymethyleneoxazolidines having the structural formula set forth hereinbefore.

Particularly advantageous results have been obtained when the aqueous solutions of polyoxymethyleneoxazolidines resulting from the reactions previously described are used without separation or purification of the biocidal compound or additional treatment other than adjustment of the concentration of the biocidal component to the desired level to protect surface-coating compositions from attack by bacteria and fungi. In addition to costing less than the purified polyoxymethyleneoxazolidines and being easier to incorporate into aqueous surface-coating compositions, the aqueous solutions, which contain 20 percent to 80 percent and preferably 40 percent to 60 percent by weight of one or more of the aforementioned polyoxymethyleneoxazolidines, provide better biocidal activity for a given concentration of the polyoxymethyleneoxazolidine in the surface-coating composition. Unlike most other aqueous surface-coating compositions that contain a biocide, the surface-coating compositions to which the aqueous polyoxymethyleneoxazolidine solutions have been added tend to become lighter in color on aging. The discovery that these polyoxymethyleneoxazolidines form stable aqueous solutions is surprising inasmuch as Carnes In U.S. Pat. No. 2,571,985 taught that polyether substituted oxazolidines tend to hydrolyze readily in aqueous solutions.

The polyoxymethyleneoxazolidines of this invention can be used to impart bacterial and fungal resistance to a wide variety of surface-coating compositions including both water-based and organic solvent-based coating systems.

The polyoxymethyleneoxazolidines are preferably used as the biocide in aqueous surface-coating compositions that contain about 10 percent to 60 percent by weight of a water-insoluble, film-forming, resinous binder that is an oleoresinous binder, a synthetic linear addition polymer, or a mixture of these binders. The useful aqueous dispersions of synthetic linear addition polymers are ordinarily prepared by the emulsion polymerization of ethylenically-unsaturated monomers. Illustrative of these polymers are polyvinyl acetate; polyvinyl butyrate; polyvinyl chloride; copolymers of vinyl acetate with vinyl chloride or acrylonitrile; copolymers of vinyl chloride with vinylidene chloride; polyethylene; polyisobutylene; polystyrene; copolymers of styrene with maleic anhydride or butadiene; copolymers of acrylonitrile with butadiene; copolymers of methacrylic acid esters of alcohols having 1 to 8 carbon atoms with vinyl acetate, vinyl chloride, acrylonitrile, or styrene; copolymers of acrylic acid esters of alcohols having 1 to 8 carbon atoms with vinyl acetate, vinyl chloride, acrylonitrile, or styrene; and mixtures therof. Suitable oleoresinous binders include drying oils, such as linseed oil, tung oil, soybean oil, dehydrated castor oil, safflower oil, or fish oil; bodied drying oils; blends of drying oils or bodied drying oils with a resin component such as limed rosin, an ester gum, or phenolic resin; oleoresinous varnishes formed by heating one of the aforementioned resins with one or more drying oils or bodied drying oils; alkyd resins, which are resinous products resulting from the reaction of a polyhydric alcohol, such as pentaerythritol or glycerol, with a dicarboxylic acid, such as phthalic anhydride, and fatty acids; and mixtures therof.

The polyoxymethyleneoxazolidines can also be used as the biocide in organic solvent-based systems that contain an oleoresinous binder as hereinbefore defined.

The addition to surface-coating compositions of as little as 0.1 percent by weight of one or more of the biocidal compounds of this invention will bring about an appreciable improvement in the resistance of the composition to attack by fungi and bacteria. Three percent or more of the biocidal compounds can be used, but these larger amounts ordinarily do not provide further improvement in the properties of the surface-coating compositions and for this reason are not usually used. The amount of the biocidal compound that will provide optimum protection for a surface-coating composition depends upon such factors as the choice of the biocidal compound, the choice of resinous binder and other ingredients of the composition and the amount of each of these materials that is used, and the application for which the coating composition is intended. In most cases 1 percent to 2 percent of polyoxymethyleneoxazolidine, based on the weight of the composition, is used to protect surface-coating compositions from attack by fungi. From 0.1 percent to 0.5 percent of a polyoxymethyleneoxazolidine, based on the weight of the composition, is preferably incorporated into aqueous surface-coating compositions to protect them from attack by bacteria.

In addition to the resinous binder and the biocidal compound, the surface-coating compositions may contain various auxiliary materials, such as pigments, extenders, solvents, dyes, defoaming agents, driers, thickeners, emulsifiers, plasticizers, other biocides, and the like in the amounts ordinarily used for these purposes.

The biocidal compounds may be incorporated into the surface-coating compositions by any suitable procedure. As has been indicated hereinbefore, the best results are obtained when aqueous solutions of the polyoxymethyleneoxazolidines are added to aqueous surface-coating compositions. Alternatively, the biocidal compounds can be combined with the pigments and other components to form a pigment phase that is mixed with the resinous binder and water or organic solvent to form the surface-coating composition.

The invention is further illustrated by the following examples.

EXAMPLE 1

A mixture of 20.2 grams (0.2 mole) of 4,4-dimethyloxazolidine and 32.4 grams (0.4 mole) of 37% aqueous formaldehyde solution was stirred at ambient temperature until a homogeneous solution was obtained. The product was an aqueous solution that contained 31.5% of water and 68.5% of 3-hydroxymethyloxymethylene-4,4-dimethyloxazolidine. The pH of an 0.1 M solution of the product was 9.8.

EXAMPLE 2

A mixture of 20.2 grams (0.2 mole) of 4,4-dimethyloxazolidine, 32.4 grams (0.4 mole) of 37% aqueous formaldehyde solution, and 6.3 grams (0.2 mole) of 95% paraformaldehyde was stirred and heated at its reflux temperature until a homogeneous solution was obtained. The solution was cooled and filtered. The resulting clear solution contained 36.6% of water and 63.4% of solids. The pH of an 0.1 M solution of the product was 10.7. The product was shown by NMR analysis to be a mixture of poly(oxymethylene)-4,4-dimethyloxazolidines containing a major amount of 3-[hydroxymethyl-di(oxymethylene)]-4,4-dimethyloxazolidine.

EXAMPLE 3

A mixture of 20.2 grams (0.2 mole) of 4,4-dimethyloxazolidine, 48.7 grams (0.6 mole) of 37% aqueous formaldehyde solution, and 6.3 grams (0.2 mole) of 95% paraformaldehyde was stirred and heated at its reflux temperature until a homogenous solution was obtained. The solution was cooled and filtered. It contained 40.4% of water and 59.6% of solids. The pH of an 0.1 M solution of the product was 10.3. The product was shown by analysis to be a mixture of poly(oxymethylene)-4,4-dimethyloxazolidines containing a major amount of 3-[hydroxymethyl-tri(oxymethylene)]-4,4-dimethyloxazolidine.

EXAMPLE 4

A. A polyvinyl acetate latex paint was prepared by mixing together the following materials:

|  | Parts by Weight |
|---|---|
| Water | 481.5 |
| 25% Aqueous solution of sodium salt of maleic anhydride/diisobutylene copolymer | 24 |
| Potassium pyrophosphate | 3 |
| Long chain fatty acid alkanolamide | 9 |
| Defoamer | 6 |
| Ethylene glycol | 75 |
| 1¼% Aqueous solution of hydroxyethylcellulose | 375 |
| Aqueous emulsion containing 55% of polyvinyl acetate | 1299 |
| Diethyl ether of diethylene glycol | 30 |
| Titanium dioxide | 690 |
| Talc | 345 |
| Calcium metasilicate | 150 |

This paint had the following properties as determined by standard paint testing procedures:

| Viscosity | 65 K.U. |
|---|---|
| Brookfield Viscosity (No. 4 spindle, 60 rpm) | 800 cps. |
| pH | 7.8 |
| Yellowness index | 3.0 |

Small amounts of the biocidal compounds of this invention or comparative biocides were added to portions of this paint.

B. An acrylic latex paint was prepared by mixing together the following materials:

|  | Parts by Weight |
|---|---|
| Water | 168 |
| Alkyl aryl ether surfactant | 6 |
| 25% Aqueous solution of sodium salt of maleic anhydride/diisobutylene copolymer | 27 |
| Defoamer | 12 |
| 2% Aqueous solution of hydroxyethylcellulose | 300 |
| Ethylene glycol | 60 |
| Titanium dioxide | 750 |
| Mica (waterground) | 90 |
| Calcium carbonate | 375 |
| Ammonium hydroxide (28%) | 6 |
| Aqueous dispersion containing 46% acrylic ester copolymer (66% ethyl acrylate, 32.5% methyl acrylate, and 1.5% acrylic acid) | 1642 |

This paint had the following properties:

| Viscosity | 72 K.U. |
|---|---|
| Brookfield Viscosity (No. 3 spindle, 60 rpm) (cps) | 1250 |
| Yellowness index | 2.6 |
| pH | 9.2 |

Small amounts of the biocidal compounds of this invention or comparative biocides were added to portions of this paint.

C. An exterior house paint was prepared by mixing together the following materials:

|  | Parts by Weight |
|---|---|
| Basic lead carbonate | 288 |
| Zinc oxide | 232 |
| Titanium dioxide (rutile) | 149 |
| Talc | 260 |
| Linseed oil | 242 |
| Bodied linseed oil | 114 |
| Mineral spirits | 114 |
| Antiskinning agent | 2 |
| Manganese naphthenate (6%) | 2.27 |
| Lead naphthenate (24%) | 11.3 |

Small amounts of the biocidal compounds of this invention or comparative biocides were added to portions of this paint.

D. The polyvinyl acetate latex paint, the acrylic latex paint, and the oil-based paint were evaluated by means of an agar diffusion assay. In this test, agar is inoculated with the test organism, the treated paint is placed in a well cut from the agar, and after incubation at 28°C. and 85–95% relative humidity, the activity of the biocide is measured by zones of inhibition. The biocidal compounds tested and the results obtained are given in the table that follows. In this table

| | ZO | = | Zone of inhibited growth in mm. |
|---|---|---|---|
| | O | = | No zone of inhibition; no growth |
| | Tr | = | Trace zone of inhibited growth |
| | — | = | Not tested |
| Bacteria | A | — | Mixed paint spoilage strains |
| | B | — | *Pseudomonas aeruginosa* |
| | C | — | *Aerobacter aerogenes* |
| Fungi | D | — | *Pullularia pullulans* |
| | E | — | *Penicillium crustosum* |
| | F | — | *Aspergillus niger* |

Each of the other monocyclic polyoxymethyleneoxazolidines disclosed herein can be used in a similar way to protect surface-coating compositions from attack by bacteria and fungi.

Activity of Polyoxymethyleneoxazolidines as Biocides in Paints

| Biocide | Paint | Test Level (%) | pH | Effect on Liquid Paint | | | Biocidal Activity | | | | | |
| | | | | Odor | Color | Viscosity | Bacteria | | | Fungi | | |
| | | | | | | | A | B | C | D | E | F |
|---|---|---|---|---|---|---|---|---|---|---|---|---|
| Product of Ex. 1 | PVA | 2 | 8.2 | None | None | None | ZO-17 | ZO-10 | ZO-11 | ZO-20 | ZO-9 | ZO-2 |

-continued

Activity of Polyoxymethyleneoxazolidines as Biocides in Paints

| Biocide | Paint | Test Level (%) | pH | Effect on Odor | Liquid Color | Paint Viscosity | Biocidal Activity |  |  |  |  |  |
|---|---|---|---|---|---|---|---|---|---|---|---|---|
|  |  |  |  |  |  |  | Bacteria |  |  | Fungi |  |  |
|  |  |  |  |  |  |  | A | B | C | D | E | F |
|  |  | 1 | 8.0 | " | " | " | ZO-11 | ZO-9 | ZO-10 | ZO-11 | ZO-4 | Tr |
|  |  | 0.5 | 7.7 | " | " | " | ZO-10 | ZO-6 | ZO-9 | ZO-5 | Tr | 0 |
|  |  | 0.1 | 7.6 | " | " | " | ZO-5 | ZO-3 | ZO-2 | Tr | 0 | 0 |
|  | Acrylic | 2 | 8.3 | " | " | " | ZO-15 | ZO-8 | ZO-10 | ZO-14 | ZO-6 | ZO-2 |
|  |  | 1 | 8.4 | " | " | " | ZO-6 | ZO-2 | ZO-2 | 0 | 0 | 0 |
|  |  | 0.5 | 8.6 | " | " | " | ZO-1 | 0 | 0 | 0 | 0 | 0 |
|  | Oil | 2 | — | " | " | " | — | — | — | ZO-8 | ZO-8 | ZO-7 |
| Product of Ex. 2 | PVA | 2 | 8.4 | Slight | None | None | ZO-18 | ZO-9 | ZO-10 | ZO-15 | ZO-15 | ZO-5 |
|  | Acrylic | 2 | 8.5 | " | " | " | ZO-13 | ZO-9 | ZO-10 | ZO-16 | ZO-11 | ZO-5 |
|  | Oil | 2 | — | None | " | " | — | — | — | ZO-10 | ZO-10 | ZO-3 |
| Product of Ex. 3 | PVA | 2 | 8.3 | None | None | None | ZO-16 | ZO-9 | ZO-12 | ZO-17 | ZO-15 | ZO-7 |
|  | Acrylic | 2 | 8.1 | " | " | " | ZO-15 | ZO-9 | ZO-12 | ZO-17 | ZO-14 | ZO-5 |
|  | Oil | 2 | — | " | " | " | — | — | — | ZO-8 | ZO-8 | ZO-4 |
| Comparative Examples |  |  |  |  |  |  |  |  |  |  |  |  |
| S-13 (Dow Chemical Co.) | PVA | 2 | 7.5 | None | None | None | ZO-13 | 0 | 0 | ZO-14 | ZO-19 | ZO-12 |
|  | Acrylic | 2 | 9.1 | " | " | " | ZO-13 | 0 | 0 | ZO-20 | ZO-11 | ZO-5 |
|  | Oil | 2 | — | " | " | " | — | — | — | ZO-20 | ZO-10 | ZO-6 |
| Bis(phenylmercuric)-dodecenyl succinate (Super Ad-it) (Tenneco Chemicals, Inc.) | PVA | 2 | 7.0 | None | None | None | ZO-19 | ZO-11 | ZO-9 | ZO-13 | ZO-10 | ZO-15 |
|  | Acrylic | 2 | 9.0 | " | " | " | ZO-17 | ZO-13 | ZO-8 | ZO-10 | ZO-3 | ZO-10 |
|  | Oil | 2 | — | " | " | " | — | — | — | ZO-17 | ZO-6 | ZO-14 |
| None | PVA | — | 7.5 | None | None | None | 0 | 0 | 0 | 0 | 0 | 0 |
|  | Acrylic | — | 9.3 | " | " | " | 0 | 0 | 0 | 0 | 0 | 0 |
|  | Oil | — | — | " | " | " | — | — | — | 0 | 0 | 0 |

What is claimed is:

1. A monocyclic polyoxymethyleneoxazolidine having the structural formula

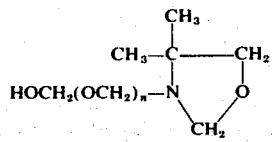

wherein $n$ represents a number in the range of 1 to 4.

2. A monocyclic polyoxymethyleneoxazolidine as defined in claim 1 that is 3-hydroxymethyloxymethylene-4,4-dimethyloxazolidine.

3. A monocyclic polyoxymethyleneoxazolidine as defined in claim 1 that is 3-[hydroxymethyl-di(oxymethylene)]4,4-dimethyloxazolidine.

4. A monocyclic polyoxymethyleneoxazolidine as defined in claim 1 that is 3-[hydroxymethyl-tri(oxymethylene)]-4,4-dimethyloxazolidine.

* * * * *